United States Patent
Li et al.

(10) Patent No.: US 12,290,086 B2
(45) Date of Patent: May 6, 2025

(54) **HYDROLYZED COMPOUND PROTEIN FOR LARVAL LARGEMOUTH BASS (*MICROPTERUS SALMOIDES*) AND USE THEREOF**

(71) Applicant: Shanghai Ocean University, Shanghai (CN)

(72) Inventors: Songlin Li, Shanghai (CN); Zhengyu Sheng, Shanghai (CN); Zhihao Han, Shanghai (CN); Naisong Chen, Shanghai (CN)

(73) Assignee: Shanghai Ocean University, Shanghai (CN)

( * ) Notice: Subject to any disclaimer, the term of this patent is extended or adjusted under 35 U.S.C. 154(b) by 495 days.

(21) Appl. No.: 17/940,107

(22) Filed: Sep. 8, 2022

(65) Prior Publication Data
US 2023/0189847 A1    Jun. 22, 2023

(30) Foreign Application Priority Data
Dec. 17, 2021    (CN) .......................... 202111551542.4

(51) Int. Cl.
| | |
|---|---|
| *A23K 50/80* | (2016.01) |
| *A23K 10/14* | (2016.01) |
| *A23K 10/22* | (2016.01) |
| *A23K 10/24* | (2016.01) |
| *A23K 10/30* | (2016.01) |
| *A23K 20/147* | (2016.01) |
| *A23K 20/163* | (2016.01) |
| *A61K 35/60* | (2006.01) |
| *A61P 3/02* | (2006.01) |

(52) U.S. Cl.
CPC .............. *A23K 50/80* (2016.05); *A23K 10/14* (2016.05); *A23K 10/22* (2016.05); *A23K 10/24* (2016.05); *A23K 10/30* (2016.05); *A23K 20/147* (2016.05); *A23K 20/163* (2016.05); *A61K 35/60* (2013.01); *A61P 3/02* (2018.01)

(58) Field of Classification Search
None
See application file for complete search history.

(56) References Cited

FOREIGN PATENT DOCUMENTS

JP    2004337003 A    * 12/2004

\* cited by examiner

*Primary Examiner* — Michael V Meller
(74) *Attorney, Agent, or Firm* — Paul D. Bianco; Fleit Intellectual Property Law

(57) ABSTRACT

A hydrolysate compound protein for larval largemouth bass (*Micropterus salmoides*) and use thereof for aquatic animal feeds. The micro-diet was formulated with the following components: 72-74 parts by weight of a hydrolyzed protein pre-mixture, 3-5 parts by weight of mixed fish soluble meal, 4-6 parts by weight of gluten flour, 2-4 parts by weight of sodium caseinate, and 0.4-0.6 parts by weight of a yeast hydrolysate, where the hydrolyzed protein pre-mixture includes white fish meal, fermented soybean meal, shrimp meal and blood meal with the weight ratio of 58-62:5-7:4-6:2-3. The compound protein is obtained by fully pulverizing the foregoing components, passing through a 100-mesh sieve, fully mixing in proportion, and being hydrolyzed with neutral protease and keratinase.

3 Claims, No Drawings

HYDROLYZED COMPOUND PROTEIN FOR LARVAL LARGEMOUTH BASS (*MICROPTERUS SALMOIDES*) AND USE THEREOF

CROSS REFERENCE TO RELATED APPLICATION

This patent application claims the benefit and priority of Chinese Patent Application No. 202111551542.4, filed on Dec. 17, 2021, the disclosure of which is incorporated by reference herein in its entirety as part of the present application.

TECHNICAL FIELD

The present disclosure relates to the technical field of aquatic animal feeds, in particular to a compound protein for larval largemouth bass (*Micropterus salmoides*) and use thereof.

BACKGROUND ART

Largemouth bass (*Micropterus salmoides*) is a typical carnivorous fish. It has become one of the important freshwater aquaculture species in China due to characteristics of rapid growth, delicious fish meat, strong disease resistance, and wide thermophily. In 2021, the annual yield of largemouth bass has exceeded 700,000 tons in China. With the continuous development of the largemouth bass aquaculture industry, the requirements for the quality of fry are also getting higher and higher. During the aquaculture, the survival rate of largemouth bass fries is extremely low, less than 3%, which has become a "bottleneck" problem that restricts the sound and sustainable development of the largemouth bass aquaculture industry.

Compared with juveniles, larval largemouth bass have a more vigorous metabolism and higher protein requirements. In addition, a typical feature of larvae is an immature digestive system, which means that larvae cannot efficiently utilize intact proteins from traditional protein sources. With the continuous development of enzymolysis technology, traditional protein sources can be enzymatically hydrolyzed through biological technology. The enzymatic protein is rich in free amino acids and small peptides that are easily digested and absorbed by larvae. However, excessive proteolysis can also inhibit the development of the digestive system of larvae. In addition, larvae have weak exercise capacity, especially at the mouth-opening stage of fry, which puts forward higher requirements for the suspensibility and stability in water of formula feed. Protein holds a leading position in micro-diet, and its proportion is as high as 70%, so the properties of protein directly affect the quality of micro-diet. At present, the research and development of micro-diet is still in its infancy, and there are no appropriate protein sources that meet the nutritional and physiological requirements and feeding habits of larval largemouth bass. Therefore, the research of high-efficiency compound proteins for larvae has caught much attention, which would provide additional scientific understanding needed for the formulation and realization of effective artificial micro-diet for largemouth bass.

At present, the aquaculture of larval largemouth bass mainly relies on feeding live preys such as *Artemia nauplii*. Long-term feeding can easily lead to the deficiency of essential nutrients in larval largemouth bass, resulting in high deformity rate and low survival rate, and lower immunity of larvae. In addition, live preys is easy to carry pathogenic bacteria, and the immune system of larvae is not fully developed and is extremely susceptible to infection by external pathogens, which in turn affects the survival rate of fries. Moreover, during the acclimatization and subsequent nursery period of larval largemouth bass, there is no suitable micro-diet for their nutritional requirements and feeding habits. They are mostly fed with the crushed and sieved aggregates of the commercial feed for juveniles. The intact proteins in the feed are not conducive to be absorbed for larvae, placing a digestive burden on larvae with underdeveloped digestive system, and thereby affecting the survival rate and feed acclimation rate of larvae. In addition, the micro-diet in the prior art is only the mutual compatibility of a plurality of proteins, which is not suitable for the typical carnivorous fish such as largemouth bass in terms of nutritional composition, and the proteins used have not been properly pretreated, which cannot meet the characteristics of the growth and development of larval largemouth bass, and cannot be effectively absorbed and utilized by larvae.

SUMMARY

In view of the problem of low survival rate of larval largemouth bass, the present disclosure provides a compound protein for larval largemouth bass and use thereof. The compound protein is formulated according to nutritional physiological needs, digestive physiology, and feeding habit of the larval largemouth bass, and can meet the nutritional requirements of the larval largemouth bass for proteins and amino acids; moreover, fitting with the digestive physiology of larvae and juveniles, the compound protein for larval largemouth bass can be used for promoting the growth, intestinal development and reduction of deformity rate of the larval largemouth bass.

To achieve the above objective, the present disclosure adopts the following technical solutions:

The present disclosure provides a hydrolyzed compound protein for larval largemouth bass, including the following components: white fish meal, fermented soybean meal, shrimp meal, and blood meal, and the weight ratio is 58-62:5-7:4-6:2-3. The compound protein is obtained by fully pulverizing the foregoing components, passing through a 100-mesh sieve, and fully mixing in proportion. The micro-diet was formulated with the following ingredients: 72-74 parts by weight of a hydrolyzed protein pre-mixture, 3-5 parts by weight of mixed fish soluble meal, 4-6 parts by weight of gluten flour, 2-4 parts by weight of sodium caseinate, and 0.4-0.6 parts by weight of a yeast hydrolysate As a preferred embodiment, the hydrolyzed protein pre-mixture is prepared by a method containing the following steps:

step 1, premixing the white fish meal, the fermented soybean meal, the shrimp meal, and the blood meal to obtain a premix, and fully mixing the premix with sterile distilled water in a solid-liquid ratio of 1:2;

step 2, weighing 2 wt % neutral protease in the premix and 1 wt % keratinase in the premix, mixing evenly, and slowly adding a mixture obtained in step 1 while stirring;

step 3, heating a mixture in step 2 in a 50° C. water bath for 30 min, and stirring the mixture once every 10 min;

step 4, putting an enzymatic hydrolysate into an air-drying oven at 105° C. for sterilization and enzyme inactivation for 30 min; and step 5, keeping drying a product after the sterilization and the enzyme inactivation at 80° C. for 12 h, and obtaining the hydrolyzed protein pre-mixture.

The present disclosure further provides a micropellet feed for larval largemouth bass, containing the foregoing compound protein for larval largemouth bass.

The present disclosure further provides use of the foregoing compound protein for larval largemouth bass or the foregoing micro-diet for larval largemouth bass in promoting the growth, intestinal development and reduction of deformity rate of larval largemouth bass.

Compared with the prior art, the present disclosure has the following beneficial effects:

1. The compound protein for larval largemouth bass provided by the present disclosure is obtained by compounding a hydrolyzed protein pre-mixture with mixed fish soluble meal, gluten flour, sodium caseinate, and a yeast hydrolysate. Through appropriate formulation of the protein, the content of fish meal in a feed is reduced, and the problem of amino acid imbalance can be solved, while the palatability of the protein is improved. The compound protein for larval largemouth bass is characteristic of high protein content, amino acid balance, excellent feed attraction property, easy digestion and absorption, excellent adhesiveness, and easy processing; a micro-diet prepared from the compound protein is used for promoting the growth, intestinal development and reduction of deformity rate of larval largemouth bass, and has an excellent use effect.

2. The present disclosure adopts the hydrolyzed protein pre-mixture obtained by full pulverization of white fish meal, fermented soybean meal, shrimp meal, and blood meal and enzymatic hydrolysis in the presence of neutral protease and keratinase, which can better satisfy the nutritional physiology at the larval stage, promote the digestion and absorption of feed proteins, and meet the nutritional and physiological requirements of the larval largemouth bass. The production practice shows that the use of the compound protein significantly improves the growth performance and survival rate of the larval largemouth bass, promotes the development of the digestive system, and substantially reduces the mortality and deformity rate during the larval period.

DETAILED DESCRIPTION OF THE EMBODIMENTS

In order to make the objectives, technical solutions and advantages of the examples of the present disclosure clearer, the technical solutions of the examples of the present disclosure will be described clearly and completely below with reference to the examples of the present disclosure. Apparently, the described examples are a part of, but not all of, the examples of the present disclosure. Based on the described examples of the present disclosure, all other examples obtained by those of ordinary skill in the art without creative efforts shall fall within the protection scope of the present disclosure.

The present disclosure relates to a compound protein for larval largemouth bass, including the following components: 72-74 parts by weight of a hydrolyzed protein pre-mixture, 3-5 parts by weight of mixed fish soluble meal, 4-6 parts by weight of gluten flour, 2-4 parts by weight of sodium caseinate, and 0.4-0.6 parts by weight of a yeast hydrolysate, where the compound protein for larval largemouth bass is obtained by fully pulverizing the foregoing components, passing through a 100-mesh sieve, and fully mixing in proportion, and the hydrolyzed protein pre-mixture includes 58-62 parts by weight of white fish meal, 5-7 parts by weight of fermented soybean meal, 4-6 parts by weight of shrimp meal, and 2-3 parts by weight of blood meal.

According to some embodiments, the compound protein for larval largemouth bass includes the following components: 73 parts by weight of the hydrolyzed protein pre-mixture, 4 parts by weight of the mixed fish soluble meal, 5 parts by weight of the gluten flour, 3 parts by weight of the sodium caseinate, and 0.5 parts by weight of the yeast hydrolysate, where the hydrolyzed protein pre-mixture includes 60 parts by weight of the white fish meal, 6 parts by weight of the fermented soybean meal, 5 parts by weight of the shrimp meal, and 2 parts by weight of the blood meal.

The present disclosure further relates to a micro-diet for larval largemouth bass, containing the foregoing compound protein for larval largemouth bass.

In the following examples, the hydrolyzed protein pre-mixture may be prepared by a method containing the following steps:

step 1, premixing the white fish meal, the fermented soybean meal, the shrimp meal, and the blood meal to obtain a premix, and fully mixing the premix with sterile distilled water in a solid-liquid ratio of 1:2;

step 2, weighing 2 wt % neutral protease in the premix and 1 wt % keratinase in the premix, mixing evenly, and slowly adding a mixture obtained in step 1 while stirring;

step 3, heating a mixture in step 2 in a 50° C. water bath for 30 min, and stirring the mixture once every 10 min;

step 4, putting an enzymatic hydrolysate into an air-drying oven at 105° C. for sterilization and enzyme inactivation for 30 min; and step 5, keeping drying a product after the sterilization and the enzyme inactivation at 80° C. for 12 h, and obtaining the hydrolyzed protein pre-mixture.

The present disclosure will be further explained and described below with reference to specific examples.

Example 1

In this example, a compound protein for larval largemouth bass was prepared. First, a hydrolyzed protein pre-mixture was prepared according to the foregoing method, fully pulverized with mixed fish soluble meal, gluten flour, sodium caseinate, and yeast hydrolysate, and passed through a 100-mesh sieve; 7.2 kg of hydrolyzed protein pre-mixture, 0.3 kg of mixed fish soluble meal, 0.4 kg of gluten flour, 0.2 kg of sodium caseinate, and 0.04 kg of yeast hydrolysate were weighed, and all components were mixed uniformly step by step (in ascending order by weight).

Example 2

In this example, a compound protein for larval largemouth bass was prepared. First, a hydrolyzed protein pre-mixture was prepared according to the foregoing method, fully pulverized with mixed fish soluble meal, gluten flour, sodium caseinate, and yeast hydrolysate, and passed through a 100-mesh sieve; 7.4 kg of hydrolyzed protein pre-mixture, 0.5 kg of mixed fish soluble meal, 0.6 kg of gluten flour, 0.4 kg of sodium caseinate, and 0.06 kg of yeast hydrolysate were weighed, and all components were mixed uniformly step by step (in ascending order by weight).

Example 3

In this example, a compound protein for larval largemouth bass was prepared. First, a hydrolyzed protein pre-mixture was prepared according to the foregoing method, fully pulverized with mixed fish soluble meal, gluten flour, sodium caseinate, and yeast hydrolysate, and passed through a 100-mesh sieve; 7.3 kg of hydrolyzed protein pre-mixture, 0.4 kg of mixed fish soluble meal, 0.5 kg of gluten flour, 0.3 kg of sodium caseinate, and 0.05 kg of yeast hydrolysate were weighed, and all components were mixed uniformly step by step (in ascending order by weight).

Example 4 Detection of Aquaculture Effect

The compound protein (the premixed protein was not treated by enzymolysis, and the proportion of each component was the same as that of the compound protein provided by the present disclosure) was used as a positive control, and the compound protein for larval largemouth bass in Example 3 was used as an experimental group; other components in the feed preparation process except the hydrolyzed protein pre-mixture feed were consistent with those of commercial feeds. The specific production steps were as follows: 8.55 kg of the foregoing compound protein, 0.3 kg of starch, 0.12 kg of soybean oil, 0.5 kg of soybean lecithin powder, 0.13 kg of vitamin premix, 0.10 kg of mineral premix, and 0.10 kg of calcium dihydrogen phosphate were weighed and fully mixed to obtain a micro-diet for larval largemouth bass.

The implementation site was located in the joint laboratory of Shanghai Ocean University and Guangdong Evergreen Feed Industry Co., Ltd. Using the current commercial feed as a negative control, and the larval largemouth bass 17 days after hatching as breeding subjects, a 4-week aquaculture experiment was carried out. The larval largemouth bass were fed 4 times a day. Three replicates were done for each treatment, and there were 2,500 fries per barrel.

The experimental data were expressed as mean±standard error (X±SEM). The experimental results were analyzed by one-way analysis of variance (ANOVA) using SPSS17.0 software. Tukey's multiple range test was chosen as a multiple comparison test and the significance level of 5% was used. The same letters following the data in the table indicate that insignificant differences.

The results showed that, compared with the control group, the compound protein for larval largemouth bass obtained in Example 3 significantly increased the final body length, final body weight and survival rate of the larval largemouth bass, and also substantially reduced the deformity rate of the larval largemouth bass; meanwhile, the above indexes in the positive control group were significantly better than those obtained by the commercial feed (negative control group) (Table 1).

Digestive system underdevelopment is a major feature of larvae, and the level of digestive enzyme activity can often effectively evaluate the development of their digestive system. This example further proved that the compound protein for larval largemouth bass in Example 3 significantly elevated the activity of pepsin, trypsin and alkaline phosphatase in the larval largemouth bass, and significantly reduced the activity of amylase, demonstrating that the compound protein for larval largemouth bass provided by the present disclosure can significantly promote the development of the digestive system. Meanwhile, the above indexes of the positive control group were significantly better than those obtained by the commercial feed (negative control group) (Table 2).

TABLE 1

Effects of the use of the compound protein on the growth indexes of larval largemouth bass

| | Negative control group | Positive control group | Experimental group |
|---|---|---|---|
| Initial body weight (mg) | 9.50 ± 0.01 | 9.50 ± 0.01 | 9.50 ± 0.01 |
| Initial body length (mm) | 9.61 ± 0.01 | 9.61 ± 0.01 | 9.61 ± 0.01 |
| Final body weight (g) | 0.68 ± 0.00$^c$ | 1.18 ± 0.09$^b$ | 1.43 ± 0.18$^a$ |
| Final body length (cm) | 2.82 ± 0.04$^c$ | 3.94 ± 0.05$^b$ | 4.28 ± 0.03$^a$ |
| Specific growth rate | 15.25 ± 0.20$^c$ | 18.56 ± 0.16$^b$ | 19.30 ± 0.12$^a$ |
| Deformity rate (%) | 41.29 ± 1.05$^c$ | 23.01 ± 1.94$^b$ | 0.48 ± 0.29$^a$ |
| Survival rate (%) | 15.95 ± 0.80$^c$ | 29.27 ± 1.18$^b$ | 35.59 ± 1.69$^a$ |

TABLE 2

Effects of the use of the compound protein on the activity of digestive enzymes of larval largemouth bass

| | Negative control group | Positive control group | Experimental group |
|---|---|---|---|
| Alkaline phosphatase (U/mgprot) | 0.56 ± 0.02$^c$ | 0.78 ± 0.03$^b$ | 1.01 ± 0.02$^a$ |
| Pepsin (U/mgprot) | 1.46 ± 0.01$^c$ | 1.96 ± 0.03$^b$ | 2.67 ± 0.10$^a$ |
| Amylase (U/gprot) | 36.14 ± 0.41$^a$ | 25.44 ± 0.98$^b$ | 19.61 ± 1.70$^c$ |
| Trypsin (U/mgprot) | 515.72 ± 12.31$^c$ | 859.76 ± 15.80$^b$ | 1851.92 ± 48.75$^a$ |

To sum up, the use of the compound protein for larval largemouth bass provided by the present disclosure in the micro-diet can significantly improve the growth performance and survival rate of larval largemouth bass, promote the development of the digestive system, and significantly reduce the deformity rate. Using the compound proteins for larval largemouth bass of Example 1 and Example 2 also obtains similar results to Example 3, and the intragroup parallel test also rules out the operating error.

What is claimed is:

1. A compound protein for larval largemouth bass (*Micropterus salmoides*), comprising the following components: 72-74 parts by weight of a hydrolyzed protein pre-mixture, 3-5 parts by weight of mixed fish soluble meal, 4-6 parts by weight of gluten flour, 2-4 parts by weight of sodium caseinate, and 0.4-0.6 parts by weight of a yeast hydrolysate, wherein the compound protein for larval largemouth bass is obtained by fully pulverizing the components, passing the components through a 100-mesh sieve, and then fully mixing in proportion the components, and wherein the hydrolyzed protein pre-mixture comprises white fish meal, fermented soybean meal, shrimp meal and blood meal, and the weight ratio is 58-62:5-7:4-6:2-3, respectively;

wherein the hydrolyzed protein pre-mixture is prepared by a method comprising the following steps:
  a) mixing the white fish meal, the fermented soybean meal, the shrimp meal, and the blood meal to obtain a premix, and then mixing the premix with sterile distilled water in a solid-liquid ratio of 1:2;
  b) adding in 2 wt. % of a neutral protease and 1 wt. % of a keratinase into the premix, mixing evenly, and then stirring to form an enzymatic premixture;
  c) heating the enzymatic premixture in b) into a 50° C. water bath for 30 min, and stirring the enzymatic premixture once every 10 min;
  d) putting an enzymatic hydrolysate into the enzymatic premixture of c) and then air drying at 105° C. for sterilization and enzyme inactivation for 30 min to obtain a resulting product; and e) then drying the resulting product after the sterilization and the enzyme inactivation in d) at 80° C. for 12 h, and then obtaining the hydrolyzed protein pre-mixture.

2. The compound protein for larval largemouth bass of claim 1, wherein the compound protein for larval largemouth bass comprises the following components: 73 parts by weight of the hydrolyzed protein pre-mixture, 4 parts by weight of the mixed fish soluble meal, 5 parts by weight of the gluten flour, 3 parts by weight of the sodium caseinate, and 0.5 parts by weight of the yeast hydrolysate, wherein the hydrolyzed protein pre-mixture comprises white fish meal, fermented soybean meal, shrimp meal and blood meal with the weight ratio of 60:6:5:2, respectively.

3. A micropellet feed for larval largemouth bass comprising the compound protein of claim 1.

* * * * *